US012589154B2

(12) United States Patent
Araki et al.

(10) Patent No.: US 12,589,154 B2
(45) Date of Patent: Mar. 31, 2026

(54) ACID TYPE SOPHOROLIPID-CONTAINING COMPOSITION WHICH IS SUPPRESSED IN BROWNING

(71) Applicant: SARAYA CO., LTD., Osaka (JP)

(72) Inventors: Michiaki Araki, Kashiwara (JP); Yoshihiko Hirata, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 1146 days.

(21) Appl. No.: 17/618,358

(22) PCT Filed: Jan. 15, 2020

(86) PCT No.: PCT/JP2020/001088
§ 371 (c)(1),
(2) Date: Dec. 10, 2021

(87) PCT Pub. No.: WO2020/250475
PCT Pub. Date: Dec. 17, 2020

(65) Prior Publication Data

US 2022/0257773 A1 Aug. 18, 2022

(30) Foreign Application Priority Data

Jun. 11, 2019 (JP) ................................ 2019-108707

(51) Int. Cl.
*A61K 47/46* (2006.01)
*A23L 33/14* (2016.01)
*A61K 8/9728* (2017.01)
*A61Q 19/00* (2006.01)
*C11D 1/36* (2006.01)

(52) U.S. Cl.
CPC .............. *A61K 47/46* (2013.01); *A23L 33/14* (2016.08); *A61K 8/9728* (2017.08); *A61Q 19/00* (2013.01); *C11D 1/36* (2013.01); *A23V 2002/00* (2013.01)

(58) Field of Classification Search
CPC .................. A61K 47/46; A61K 8/9728; A61K 2800/805; A61K 8/498; A61K 8/604; A61K 2800/10; A61K 2800/26; A23L 33/14; A23L 29/04; A23L 29/10; A23L 29/00; A61Q 19/00; A61Q 19/10; C11D 1/36; A23V 2002/00; C07H 1/00; C07H 15/04; C12P 19/44
See application file for complete search history.

(56) References Cited

U.S. PATENT DOCUMENTS

| | | | |
|---|---|---|---|
| 5,417,879 | A | 5/1995 | Hall et al. |
| 5,688,930 | A | 11/1997 | Bertho et al. |
| 5,756,471 | A | 5/1998 | Hillion et al. |
| 5,981,497 | A | 11/1999 | Maingault |
| 6,057,302 | A | 5/2000 | Borzeix |
| 10,065,982 | B2 | 9/2018 | Hirata et al. |
| 10,688,031 | B2 | 6/2020 | Ito et al. |
| 10,752,650 | B2 | 8/2020 | Araki et al. |
| 11,312,928 | B2 | 4/2022 | Okada et al. |
| 2004/0171512 | A1 | 9/2004 | Furuta et al. |
| 2011/0237531 | A1 | 9/2011 | Yanagisawa et al. |
| 2012/0142621 | A1 | 6/2012 | Falus et al. |
| 2012/0220464 | A1 | 8/2012 | Giessler-Blank et al. |
| 2013/0035403 | A1 | 2/2013 | Schaffer et al. |
| 2014/0349902 | A1 | 11/2014 | Allef et al. |
| 2015/0056658 | A1 | 2/2015 | Schaffer et al. |
| 2015/0056659 | A1 | 2/2015 | Schaffer et al. |
| 2015/0056660 | A1 | 2/2015 | Schaffer et al. |
| 2015/0056661 | A1 | 2/2015 | Schaffer et al. |
| 2015/0112049 | A1 | 4/2015 | Hirata et al. |
| 2015/0203443 | A1 | 7/2015 | Klostermann et al. |
| 2015/0336999 | A1 | 11/2015 | Jourdier et al. |
| 2016/0280733 | A1 | 9/2016 | Araki et al. |
| 2016/0324747 | A1 | 11/2016 | Ito et al. |
| 2018/0256489 | A1 | 9/2018 | Silberstein et al. |
| 2020/0032168 | A1 | 1/2020 | Okada et al. |

FOREIGN PATENT DOCUMENTS

| | | | |
|---|---|---|---|
| CN | 102492753 | A | 6/2012 |
| CN | 102695796 | A | 9/2012 |
| CN | 104968325 | A | 10/2015 |
| CN | 105593370 | A | 5/2016 |
| CN | 105661630 | A | 6/2016 |
| CN | 106282264 | A | 1/2017 |
| EP | 0499434 | A1 | 8/1992 |
| EP | 2351847 | A1 | 8/2011 |
| JP | S56-022399 | A | 3/1981 |

(Continued)

OTHER PUBLICATIONS

Ashby et al., "Property control of sophorolipids: influence of fatty acid substrate and blending," *Biotechnol. Lett.*, 30(6): 1093-1100 (2008).

(Continued)

*Primary Examiner* — Snigdha Maewall

(74) *Attorney, Agent, or Firm* — Leydig, Voit & Mayer, Ltd.

(57) ABSTRACT

The present invention provides an acidic sophorolipid-containing composition with suppressed browning and a method for producing the composition. The acidic sophorolipid-containing composition with suppressed browning according to the present invention is characterized in that a filtrate of a hydrolysate of a composition containing lactonic sophorolipid and acidic sophorolipid, i.e., a filtrate of the acidic sophorolipid-containing composition, has at least one of the following features (1) and (2):

(1) hue value (Abs. 440): 5 or less; and (2) ethanol-insoluble content: less than 3 mass %.

7 Claims, No Drawings

(56) References Cited

FOREIGN PATENT DOCUMENTS

| | | | |
|---|---|---|---|
| JP | H04-170499 | A | 6/1992 |
| JP | H05-059394 | A | 3/1993 |
| JP | H07-118284 | A | 5/1995 |
| JP | H10-501260 | A | 2/1998 |
| JP | H11-508549 | A | 7/1999 |
| JP | 2002-045195 | A | 2/2002 |
| JP | 2003-009896 | A | 1/2003 |
| JP | 2003-013093 | A | 1/2003 |
| JP | 2006-070231 | A | 3/2006 |
| JP | 2006-083238 | A | 3/2006 |
| JP | 2006-212086 | A | 8/2006 |
| JP | 2008-247845 | A | 10/2008 |
| JP | 2009-062288 | A | 3/2009 |
| JP | 2009-531310 | A | 9/2009 |
| JP | 2009-275145 | A | 11/2009 |
| JP | 2013-511266 | A | 4/2013 |
| JP | 2014-117240 | A | 6/2014 |
| JP | 2014-150774 | A | 8/2014 |
| JP | 2015-100290 | A | 6/2015 |
| JP | 2016-000017 | A | 1/2016 |
| JP | 2016-160244 | A | 9/2016 |
| JP | 6157524 | B2 | 7/2017 |
| WO | WO 2007/130738 | A1 | 11/2007 |
| WO | WO 2010/050413 | A1 | 5/2010 |
| WO | WO 2011/061032 | A1 | 5/2011 |
| WO | WO 2011/127101 | A1 | 10/2011 |
| WO | WO 2013/129667 | A1 | 9/2013 |
| WO | WO 2015/034007 | A1 | 3/2015 |

OTHER PUBLICATIONS

Cooper et al., "Production of a Biosurfactant from Torulopsis bombicola," *Appl. Environ. Microbiol.*, 47(1): 173-176 (1984).

Gorin et al., "Hydroxy Fatty Acid Glycosides of Sophorose from Torulopsis Magnoliae," *Canadian Journal of Chemistry*, 39(4): 846-855 (1961).

Japanese Patent Office, International Search Report in International Patent Application No. PCT/JP2020/001088 (Mar. 10, 2020).

Health Science Research Group, "Use Alternative Methods to Improve the Eye Irritation of Cosmetic Ingredients," Workshop on OECD Guidelines for Testing of Chemicals, Guidelines for Evaluation (1998).

Asmer et al., "Microbial production , structure elucidation and bioconversion of sophorose lipids," *J. American Oil Chem. Soc.*, 65(9): 1460-1466 (1988).

Brakemeier et al., *Candida bombicola*: production of novel alkyl glycosides based on glucose/2-dodecanol, *Appl. Microbiol. Biotechnol.*, 50(2): 161-166 (1998).

Cavalero et al., "The effect of medium composition on the structure and physical state of sophorolipids produced by *Candida bombicola* ATCC 22214," *J. Biotech.*, 103(1): 31-41 (2003).

Daniel et al., "Sophorolipid Production with High Yields on Whey Concentrate and Rapeseed Oil without Consumption of Lactose," *Biotech. Lett.*, 20(8): 805-807 (1998).

Daverey, "Production, Characterization, and Properties of Sophorolipids from the Yeast *Candida bombicola* using a Low-cost Fermentative Medium," *Appl. Biochem. Biotechnol.*, 158(3): 663-674 (2009).

Davila et al., "Kinetics and balance of a fermentation free from product inhibition: sophorose lipid production by *Candida bombicola,*" *Appl. Microbiol. Biotechnol.*, 38: 6-11 (1992).

Davila et al., "Identification and determination of individual sophorolipids in fermentation products by gradient elution high performance liquid chromatography with evaporative light-scattering detection," *J. Chromatogr.*, 648(1): 139-149 (1993).

Deshpande et al., "Evaluation of sophorolipid biosurfactant production by *Candida bombicola* using animal fat," *Bioresource Tech.*, 54(2): 143-150 (1995).

Gu et al., "A Study of the Scale-Up of Reversed-Phase Liquid Chromatography," *Separation and Purification Technology*, 15(1): 41-58 (1999).

Hirata et al., "Natural synergism of acid and lac tone type mixed sophorolipids in interfacial activities and cytotoxicities," *J. Oleo Sci.*, 58(11): 565-572 (2009).

Hommel, "Formation and physiological role of biosurfactants produced by hydrocarbon-utilizing microorganisms. Biosurfactants in hydrocarbon utilization," *Physiology of Biodegradative Microorganisms*, 1(2-3): 107-119 (1990).

Liu et al., "Progress on biosynthesis and application of sophorolipids," *Food Drug.*, 1(11): 51-55 (2009).

Ma et al., "Effects of nitrogen sources on production and composition of sophorolipids by *Wickerhamiella domercqiae* var. sophorolipid CGMCC 1576," *Appl. Microbiol. Biotechnol.*, 91(6): 1623-1632 (2011).

Nuñez et al., "LC/MS analysis and lipase modification of the sophorolipids produced by Rhodotorula bogoriensis," *Biotechnol. Lett.*, 26(13): 1087-1093 (2004).

Okamoto, "Recent developments of Draize eye test alternative in Japan," *Fragrance Journal*, 2: 67-71 (2005).

Rau et al., "Sophorolipids: a source for novel compounds," *Industrial Crops Products*, 13(2): 85-92 (2001).

Saerens et al., "One-step production of unacetylated sophorolipids by an acetyltransferase negative *Candida bombicola,*" *Biotechnol. Bioeng.*, 108(12): 2923-2931 (2011).

Shah et al., "Sophorolipids, microbial glycolipids with anti-human immunodeficiency virus and sperm-immobilizing activities," *Antimicrob. Agents Chemother.*, 49(10): 4093-4100 (2005).

Shah et al., "Utilization of Restaurant Waste Oil as a Precursor for Sophorolipid Production," *Biotechnology Prog.*, 23(2): 512-515 (2007).

Song et al., "Structure characterization and physi-chemical properties of sophorolipid biosurfactants," *Environmental Chemistry*, 30(8): 1474-1479 (2011).

Tulloch et al., "A new hydroxy fatty acid sophoroside from *Candida bogoriensis,*" *Can. J. Chem.*, 46(3): 345-348 (1968).

Tulloch et al., "Structure and reactions of lactonic and acidic sophorosides of 17-hydroxyoctadecanoic acid," *Can. J. Chem.*, 46(21): 3337-3351 (1968).

Van Bogaert et al. "Microbial production and application of sophorolipids," *Appl. Microbiol. Biotechnol.*, 76(1): 23-34 (2007).

Yatim, "Biotransformation of Palm Olein into Sophorolipid Biosurfactant," Doctor of Philosophy Thesis, University of New South Wales (2008).

Zhou et al., "Production of sophorose lipids by Torulopsis bombicola from safflower oil and glucose," *J. American Oil Chem Soc.*, 69(1): 89-91 (1992).

Zhou et al., "Supramolecular Assemblies of a Naturally Derived Sophorolipid," *Langmuir*, 20: 7926-7932 (2004).

China National Intellectual Property Administration, Office Action in Chinese Patent Application No. 201480054091.5 (Oct. 29, 2018).

China National Intellectual Property Administration, First Office Action in Chinese Patent Application No. 201880016429.6 (Oct. 19, 2020).

European Patent Office, Extended European Search Report in European Patent Application No. 14843085.3 (Feb. 23, 2017).

European Patent Office, Extended European Search Report in European Patent Application No. 14834955.8 (Nov. 16, 2016).

European Patent Office, Communication Pursuant to Article 94(3) EPC in European Patent Application No. 14834955.8 (Jul. 21, 2017).

European Patent Office, Third Party Observations for European Patent Application No. 14834955.8 (Jun. 19, 2020).

European Patent Office, Communication Pursuant to Rule 114(2) EPC in European Patent Application No. 14834955.8 (Jun. 19, 2020).

Japanese Patent Office, International Search Report in International Patent Application No. PCT/JP2014/070788 (Nov. 11, 2014).

Japanese Patent Office, Written Opinion of the International Searching Authority in International Patent Application No. PCT/JP2014/070788 (Nov. 11, 2014).

Japanese Patent Office, International Search Report in International Patent Application No. PCT/JP2014/073356 (Dec. 2, 2014).

(56) References Cited

OTHER PUBLICATIONS

Japanese Patent Office, Written Opinion of the International Searching Authority in International Patent Application No. PCT/JP2014/073356 (Dec. 2, 2014).
Japanese Patent Office, International Search Report in International Patent Application No. PCT/JP2018/008865 (Apr. 3, 2018).
Japanese Patent Office, Notice of Reasons for Refusal in Japanese Patent Application No. 2018-568976 (Jan. 22, 2019).
Baccile et al., "Practical Methods to Reduce Impurities for Gram-Scale Amounts of Acidic Sophorolipid Biosurfactants," *European Journal of Lipid Science and Technology*, 115(12): 1404-1412 (2013).
European Patent Office, Extended European Search Report in European Patent Application No. 20822640.7 (Jun. 9, 2023).
U.S. Appl. No. 14/382,480, filed Sep. 2, 2014.
U.S. Appl. No. 14/911,174, filed May 23, 2016.
U.S. Appl. No. 15/061,330, filed Mar. 4, 2016.
U.S. Appl. No. 16/491,511, filed Sep. 5, 2019.

ACID TYPE SOPHOROLIPID-CONTAINING COMPOSITION WHICH IS SUPPRESSED IN BROWNING

TECHNICAL FIELD

The present invention relates to an acidic sophorolipid-containing composition with suppressed browning and to a method for producing the acidic sophorolipid-containing composition. Further, the present invention relates to a method for inhibiting browning of an acidic sophorolipid-containing composition.

BACKGROUND ART

Biosurfactants ("BS"), which are surfactants of biological origin, are known to be biodegradable and safe. Sophorolipid ("SL"), which is a glycolipid-type BS, is a fermentation product obtained from fermentation by yeast. SL can be easily produced, for example, by inoculating yeast on a liquid medium containing a carbon source such as a saccharide for example glucose, and a vegetable oil and fat, and stirring the medium while aerating it at a mild temperature and under pressure. SL has higher productivity (for example, about 100 g/L) than other BS.

However, since fermentation by-products (various organic acids and salts thereof, pigments, etc.) are also produced at the same time during the SL fermentation production process, unpurified SL extracted after completion of fermentation has a brownish color with a peculiar odor. Further, since the SL obtained by fermentation is a mixture of lactonic SL and acidic SL, the mixture is further subjected to alkaline hydrolysis (saponification) to form a safer acidic SL (see, for example, Patent Literature (PTL) 1 to Patent Literature (PTL) 3 etc.). On the other hand, acidic SL obtained by conventional saponification has a brown color darker than or as dark as that before treatment. When the acidic SL is allowed to stand at temperatures of 50 to 100° C., there also arises a problem that browning further progresses and increases, although no structural change occurs in acidic SL. Therefore, since incorporation of such unpurified acidic SL into products, such as medicines, quasi-drugs, foods, and cosmetics, has an adverse effect on the appearance and storage stability of the products, further purification is required.

In general, the most difficult and costly part of the production of fermentation products is the purification process. Many of the previously reported methods for purification of SL comprise extraction by adding an equivalent amount of hexane and ethyl acetate to a liquid culture medium (e.g., Non-Patent Literature (NPL) 1). However, the SL obtained by this method retains a peculiar odor. A method for purifying SL as a white substance is also reported (Non-Patent Literature (NPL) 2). In NPL 2, the liquid culture medium itself was freeze-dried, ethyl acetate was added to the dried material, and the resulting mixture was stirred at 30° C. for 2 days. After distilling off ethyl acetate, the mixture was crystallized in hexane. However, this method is difficult to put into practice because it is necessary to add a flammable organic solvent and then allow the solution to stand for several days. Furthermore, these methods require removal or recovery of an organic solvent from the recovered liquid. This requires special equipment and energy for the treatment of waste liquid containing an organic solvent, leading to higher costs. In addition, the use of such an organic solvent requires it to be strictly managed from the standpoint of environmental impact and adverse health effects. Furthermore, if an organic solvent remains in the obtained SL, its application to food products and cosmetics becomes difficult. On the other hand, a method using reversed-phase chromatography as a purification method has also been proposed (see, for example, Patent Literature (PTL) 2 and Patent Literature (PTL) 3). However, this method is time-consuming and costly. Thus, methods known until now can be used for basic research, but are insufficient for industrial application or general industrial use, and further research is necessary.

From the standpoint of general industrial use, production and purification of SL must be a process that is inexpensive and safe. In the case of general-purpose chemical products, the cost aspect becomes particularly important. Furthermore, at present, in addition to the biodegradability of products after use, it is important to establish a safer manufacturing process, including for the raw materials, from the standpoint of life-cycle assessment (LCA). For this reason, it is also desirable to establish a method of manufacturing SLs derived from living organisms without using or discharging harmful organic solvents.

Accordingly, establishment of a method for producing acidic SL with a high yield and at low cost without using harmful organic solvents is expected to dramatically advance industrial application of SL as a new material that is derived from living organisms, is safe, and has excellent biodegradability.

CITATION LIST

Patent Literature

PTL 1: JP2006-70231A
PTL 2: WO2013/129667
PTL 3: WO2015/034007

Non-Patent Literature

NPL 1: D. G. Cooper and D. A. Paddock, Appl. Environ. Microbiol., 47, 173-176, 1984
NPL 2: R. D. Ashby, D. K. Y. Solaiman, and T. A. Foglia, Biotechnol. Lett., 30, 1093-1100, 2008

SUMMARY OF INVENTION

Technical Problem

An object of the present invention is to provide an acidic SL-containing composition that has suppressed browning, and a method for producing the composition. More specifically, an object of the present invention is to provide a hydrolysis method for more easily and inexpensively preparing an acidic SL-containing composition with suppressed browning.

Solution to Problem

In order to solve the above problem, the present inventors conducted intensive research. As a result, the inventors found that when an unpurified acidic SL-containing product (a composition containing lactonic SL and acidic SL) obtained in the fermentation generation process is hydrolyzed under a temperature condition of 80° C. or less using an alkaline agent in an amount of 0.8 to 1.5 g eq. relative to the saponification value of the composition, the obtained hydrolysate is a composition containing acidic SL in a proportion of 78 mass % or more, based on the total amount of lactonic SL and acidic SL taken as 100 mass %, and has significantly suppressed browning such that a filtrate of the hydrolysate has a hue value (Abs. 440) of 5 or less. The inventors further found that the obtained acidic SL-containing composition has stably suppressed browning over time, as is clear from the fact that the filtrate has no significant increase in hue value (Abs. 440) even after being allowed to stand in the dark at 50° C. for 1 month. Further, the inventors confirmed that when the hydrolysate (acidic SL-containing composition) is adjusted to a pH of 6 to 9, the obtained composition (the composition having a pH of 6 to 9) has even more stably suppressed browning. The inventors conducted further research based on these findings and have accomplished the present invention.

More specifically, the present invention provides an acidic SL-containing composition (a hydrolysate of a composition containing lactonic SL and acidic SL) with suppressed browning, and a method for producing the composition. The present invention also provides a hydrolysis method for preparation of the acidic SL-containing composition with suppressed browning. Further, the present invention provides a method for inhibiting browning of the acidic SL-containing composition. The acidic SL-containing product with suppressed browning of the present invention is also referred to below as a "acidic SL-containing composition with browning resistance" or a "hydrolysate with browning resistance."

(I) Acidic SL-Containing Composition with Suppressed Browning (Hydrolysate of Composition Containing Lactonic SL and Acidic SLs)

(I-1) A hydrolysate of a composition containing lactonic SL and acidic SL, the acidic SL being present in a proportion of 78 mass % or more, based on the total amount of the lactonic SL and the acidic SL taken as 100 mass %, wherein the filtrate of the hydrolysate has the following features (1) and (2):

(1) the hue value (Abs. 440) is 5 or less, preferably 2 or less, and more preferably 1.5 or less; and
(2) the ethanol-insoluble content is less than 3 mass %, preferably 2 mass % or less, and more preferably 1.5 mass % or less.

The "filtrate of the hydrolysate" as referred to herein means a filtrate obtained by adjusting a hydrolysate of a composition containing lactonic SL and acidic SL to room temperature (25±5° C.) and filtering the resulting hydrolysate through a filter with a pore size of 0.45 μm.

The "hue value (Abs. 440)" is a value obtained by dissolving the filtrate in distilled water to achieve an ethanol-soluble content of 3 mass %, filtering the diluted aqueous solution through a filter with a pore diameter of 0.45 μm, measuring the absorbance of the obtained filtrate at a wavelength of 440 nm by using an infrared/UV-visible spectrophotometer, and multiplying the absorbance (Abs. 440) by 10.

(I-2) The hydrolysate according to (I-1), wherein the filtrate of the hydrolysate further has the following feature (3):

(3) the hue value (Abs. 440) after being allowed to stand at 50° C. for 1 month is 10 or less, preferably 5 or less, and more preferably 3 or less.

(I-3) The hydrolysate according to (I-1) or (I-2), wherein the filtrate of the hydrolysate further has the following feature (4):

(4) the liquid property (pH) is a pH of 6 to 9, preferably a pH of 7 to 9, and more preferably a pH of 7.5 to 8.5.

(I-4) The hydrolysate according to any of (I-1) to (I-3), wherein the filtrate of the hydrolysate further has at least one feature selected from (5) and (6):

(5) saponification value: 1 to 25 mgKOH/g; and
(6) ignition residue: 16 mass % or less.

(II) Method for Producing Acidic SL-Containing Composition (Hydrolysate of a Composition Containing Lactonic SL and Acidic SL) with Suppressed Browning (II-1) A method for producing a hydrolysate of a composition containing lactonic SL and acidic SL, the method comprising the following step (a):

(a) hydrolyzing a composition containing lactonic SL and acidic SL at 80° C. or less using an alkaline agent in an amount of 0.8 to 1.5 g eq. relative to the saponification value of the composition to obtain a hydrolysate whose filtrate has the following features (1) and (2):
(1) the hue value (Abs. 440) is 5 or less, preferably 2 or less, and more preferably 1.5 or less; and
(2) the ethanol-insoluble content is less than 3 mass %, preferably 2 mass % or less, and more preferably 1.5 mass % or less, wherein the "filtrate of the hydrolysate" refers to a filtrate obtained by adjusting a hydrolysate of a composition containing lactonic SL and acidic SL to room temperature (25±5° C.) and filtering the adjusted hydrolysate through a filter with a pore size of 0.45 μm, and the "hue value (Abs. 440)" is a value obtained by dissolving the filtrate in distilled water to achieve an ethanol-soluble content of 3 mass %, filtering the diluted aqueous solution through a filter with a pore diameter of 0.45 μm, measuring the absorbance of the obtained filtrate at a wavelength of 440 nm using an infrared/UV-visible spectrophotometer, and multiplying the absorbance (Abs. 440) by 10.

(II-2) The production method according to (II-1), further comprising the following step (b):

(b) adjusting the hydrolysate obtained in step (a) or the filtrate of the hydrolysate to a pH of 6 to 9.

(II-3) The production method according to (II-1) or (II-2), wherein the hydrolysate is an acidic SL-containing composition containing acidic SL in a proportion of 78 mass % or more, based on the total amount of lactonic SL and acidic SL taken as 100 mass %.

(III) Hydrolysis Method for Producing Acidic SL-Containing Composition with Suppressed Browning (III-1) A method for hydrolyzing a composition containing lactonic SL and acidic SL to produce an acidic SL-containing composition with suppressed browning, the method comprising the following step (a):

(a) hydrolyzing a composition containing lactonic SL and acidic SL at 80° C. or less using an alkaline agent in an amount of 0.8 to 1.5 g eq. relative to the saponification value of the composition to obtain a hydrolysate whose filtrate has the following features (1) and (2):
(1) the hue value (Abs. 440) is 5 or less, preferably 2 or less, and more preferably 1.5 or less; and
(2) the ethanol-insoluble content is less than 3 mass %, preferably 2 mass % or less, and more preferably 1.5 mass % or less.

The "filtrate of the hydrolysate" as referred to herein is a filtrate obtained by adjusting the hydrolysate of the composition containing lactonic SL and acidic SL to room temperature (25±5° C.) and filtering the adjusted hydrolysate through a filter with a pore size of 0.45 μm.

The "hue value (Abs. 440)" is a value obtained by dissolving the filtrate in distilled water to achieve an ethanol-soluble content of 3 mass %, filtering the resulting solution through a filter with a pore size of 0.45 μm, measuring the absorbance of the obtained filtrate at a wavelength of 440 nm by using an infrared/UV-visible spectrophotometer, and multiplying the absorbance (Abs. 440) by 10.

(III-2) The method according to (III-1), further comprising the following step (b):

(b) adjusting the hydrolysate obtained in step (a) or the filtrate of the hydrolysate to a pH of 6 to 9.

(IV) Use of Acidic SL-Containing Composition with Suppressed Browning (Hydrolysate of Composition Containing Lactonic SL and Acidic SL)

(IV-1) An anionic surfactant comprising the hydrolysate (acidic SL-containing composition with suppressed browning) according to any one of (I-1) to (I-4), or a processed product thereof as an active ingredient.

(IV-2) A perfumery or cosmetic, a food or drink, a detergent, a quasi-drug, a pharmaceutical, or an additive therefor, comprising the hydrolysate (acidic SL-containing composition with suppressed browning) of any one of (I-1) to (I-4) or a processed product thereof as an active ingredient.

(IV-3) A method for producing a perfumery or cosmetic, a food or drink, a detergent, a quasi-drug, or a pharmaceutical, the method comprising the steps of mixing a third component for use in the manufacture of perfumery and cosmetics, foods and drinks, detergents, quasi-drugs, or pharmaceuticals into the hydrolysate (acidic SL-containing composition with suppressed browning) of any one of (I-1) to (I-4) or a processed product thereof; and forming the resulting mixture into a product.

(IV-4) The perfumery or cosmetic, food or drink, detergent, quasi-drug, pharmaceutical, or additive thereof of (IV-2), wherein the perfumery or cosmetic, food or drink, detergent, quasi-drug, and pharmaceutical are all applied to the human body.

Advantageous Effects of Invention

According to the production method and the hydrolysis method of the present invention, an acidic SL-containing composition with suppressed browning can be easily obtained as a hydrolysate of a composition containing lactonic SL and acidic SL at low cost. Specifically, the method of the present invention can produce an acidic SL-containing composition that has suppressed browning more stably than conventional methods, such as a method of hydrolyzing a composition containing lactonic SL and acidic SL at room temperature using an alkaline agent in an amount of 2 to 4 g eq. relative to the saponification value of the composition. Since the present invention can produce an acid SL-containing composition that has stably suppressed browning without using a purification method using an organic solvent or column chromatography, a highly safe acidic SL-containing composition with browning resistance can be obtained conveniently and inexpensively.

DESCRIPTION OF EMBODIMENTS (I) Sophorolipid

Sophorolipid (SL) is generally a glycolipid consisting of sophorose or a sophorose whose one or more hydroxy groups are acetylated, and a hydroxy fatty acid. Sophorose is a sugar consisting of two glucose molecules bound through a β1→2 bond. Hydroxyl fatty acid is a fatty acid having a hydroxy group. SL is roughly classified into acidic SL and lactonic SL. Acidic SL is a sophorolipid in which the carboxy group of the hydroxy fatty acid is free. Lactonic SL is a sophorolipid in which the carboxy group of the hydroxy fatty acid is bound to the sophorose in the molecule. The SL obtained from a species of yeast (SL-producing yeast) through fermentation is usually a mixture of SL represented by the following formula (1) and SL represented by the following formula (2), and is obtained as a collection of 30 or more types of structural homologues, such as those having different fatty acid chain lengths ($R_2$), those acetylated or protonated at the 6'-position ($R_3$) and the 6"-position ($R_4$) of the sophorose, and those esterified at one of the 3'-, 4'-, 2"-, 3"-, and 4"-positions ($R_5$) of the sophorose.

(1)

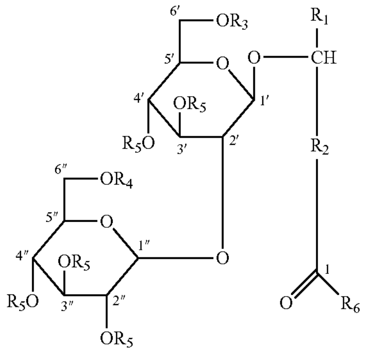

(In formula (1), $R_1$ represents a hydrogen atom or a methyl group;

$R_3$ and $R_4$ are the same or different and independently represent a hydrogen atom or an acetyl group;

all $R_5$ are hydrogen atoms, or one of the five $R_5$ is a saturated or unsaturated fatty acid residue that may have hydroxy, and the rest of the four $R_5$ are all hydrogen atoms;

$R_2$ is a saturated aliphatic hydrocarbon chain, or an unsaturated aliphatic hydrocarbon chain having at least one double bond, which may have one or more substituents; and $R_5$ is a hydroxy group).

(2)

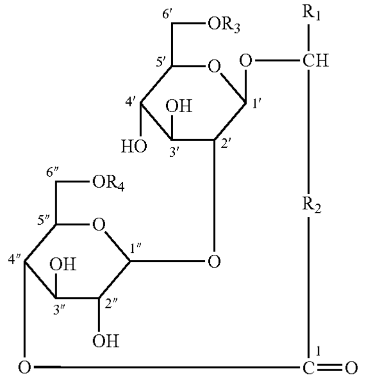

(In formula (2), $R_1$ to $R_4$ are as defined in formula (1)).

The SL obtained through fermentation by an SL-producing yeast may contain a dimer in which $R_6$ at the C-1 position of one of the acidic SLs represented by formula (1), which is a saturated or unsaturated fatty acid residue in which one $R_5$ group may have a hydroxy group, is bound to one $R_7$ of acidic SL represented by formula (3) to form a single bond.

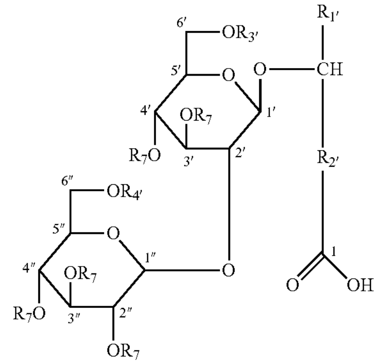

(3)

(In formula (3), $R_{1'}$ is a hydrogen atom or a methyl group;

$R_{3'}$ and $R_{4'}$ are the same or different and represent a hydrogen atom or an acetyl group;

$R_{2'}$ is a saturated aliphatic hydrocarbon chain or an unsaturated aliphatic hydrocarbon chain having at least one double bond and may have one or more substituents; and one $R_7$ is bound to $R_6$ of the acidic SL represented by formula (1) to form a single bond, and the rest of the $R_7$ are all hydrogen atoms.)

In formulas (1) to (3), the number of carbons in the saturated or unsaturated aliphatic hydrocarbon chain represented by $R_2$ or $R_2$' is not limited, but is usually 9 to 20, preferably 9 to 18, more preferably 11 to 16, and particularly preferably 14 to 16. The saturated aliphatic hydrocarbon chain can be, for example, a linear or branched chain alkylene group, and is preferably a linear alkylene group. Examples of the unsaturated aliphatic hydrocarbon chain include alkenylene groups having 1 to 3 double bonds. The unsaturated aliphatic hydrocarbon chain is preferably an alkenylene group having 1 to 2 double bonds, and more preferably an alkenylene group having 1 double bond. There is no limitation on the substituent of the saturated or unsaturated aliphatic hydrocarbon chain represented by $R_2$ or $R_2$'. Examples of substituents include halogen atoms, a hydroxy group, lower ($C_{1-6}$) alkyl groups, halo-lower ($C_{1-6}$) alkyl groups, hydroxy lower ($C_{1-6}$) alkyl groups, halo-lower ($C_{1-6}$) alkoxy groups, and the like. Examples of halogen atoms or halogen atoms bound to alkyl or alkoxy groups include a fluorine atom, a chlorine atom, a bromine atom, and an iodine atom.

Examples of saturated fatty acid residues represented by $R_5$ in formula (1) include $C_{12-20}$ linear fatty acid residues (lauric acid residue, myristic acid residue, pentadecylic acid residue, palmitic acid residue, margaric acid residue, stearic acid residue, and arachidic acid residue), preferably $C_{14-20}$, more preferably $C_{16-20}$, even more preferably $C_{16-18}$ linear fatty acid residues, and particularly preferably $C_{16}$ palmitic acid residue and $C_{18}$ stearic acid residue. Examples of unsaturated fatty acid residues include $C_{12-20}$ linear fatty acid residues having 1 to 3 double bonds. The number of double bonds is preferably 1 to 2 and more preferably 1. The number of carbon atoms is preferably 16 to 20, more preferably 16 to 18, and particularly preferably 18. Preferable examples of unsaturated fatty acid residues include $C_{16}$ palmitoleic acid residue having one double bond; $C_{18}$ oleic acid residue or vaccenic acid residue having one double bond (preferably oleic acid residue); $C_{18}$ linoleic acid residue having two double bonds; $C_{18}$ linolenic acid residue (9,12,15), linolenic acid residue (6,9,12), and eleostearic acid residue having three double bonds; and $C_{20}$ linolenic acid residue (9,12,15), linolenic acid residue (6,9,12), and eleostearic acid residue having two double bonds. More preferably, the unsaturated fatty acid residue is $C_{16}$ palmitoleic acid residue having one double bond and $C_{18}$ oleic acid residue having one double bond, particularly preferably a $C_{18}$ oleic acid residue having one double bond.

These fatty acid residues may have hydroxyl or may not have hydroxy. When the fatty acid residues have hydroxy, the number of hydroxy is 1 or 2, preferably 1. Further, the hydroxy may be present, for example, at the ω-position or ω-1-position in the fatty acid residue. In acidic SL (1), when $R_5$ is a saturated or unsaturated fatty acid residue that may have hydroxy, —$OR_5$ may be present at any of the 3', 4', 2", 3", and 4"-positions of the sophorose ring. More specifically, acidic SL (1) includes an SL compound in which an —$OR_5$ group having $R_5$ that is the fatty acid residue described above is present at one of these positions. More preferably, acidic SL (1) is a compound (1) in which —$OR_5$ having $R_5$ that is a saturated or unsaturated fatty acid residue that may have hydroxy is present at the 4"-position of the sophorose ring.

As described above, in a liquid culture obtained through fermentation by an SL-producing yeast, SL is usually present as a mixture of acidic SL (monomeric SL shown in formula (1)) and lactonic SL (monomeric SL shown in formula (2)). Among those, since the lactonic SL is a nonionic oily substance and is extremely insoluble in water by itself, it is undesirable to have lactonic SL in a high proportion because it causes a sophorolipid mixture to be water-insoluble as a whole. On the other hand, it is preferable to have acidic SL in a high proportion because it is chemically stable as compared to lactonic SL. The ratio of acidic SL to lactonic SL in the liquid culture is not limited but is typically such that the amount of acidic SL is less than 65 mass % and the amount of lactonic SL is 35 mass % or more (dry weight ratio), based on the total amount of acidic SL and lactonic SL contained in the culture medium taken as 100 mass %. Preferably, the ratio of acidic SL to lactonic SL in the culture medium can be in the range of 40:60 to 10:90 (dry weight ratio).

Examples of preferable SL-producing yeast include *Candida bombicola*. The *Candida* genus has been renamed the *Starmerella* genus. This yeast is an SL-producing yeast known to produce a significant amount of (acidic and lactonic) SL (Canadian Journal of Chemistry, 39, 846 (1961) (note: the *Torulopsis* genus described in the document belongs to the *Candida* genus, but is currently classified into the *Starmerella* genus, as described above); Applied and Environmental Microbiology, 47, 173 (1984); etc.). *Candida* (*Starmerella*) *bombicola* has been deposited with, and is available from, the American Type Culture Collection (ATCC), which is a bioresource bank (*Candida bombicola* ATCC22214). Other SL-producing yeast that belongs to the *Candida* genus (*Starmerella* genus) and is known to produce (acidic and lactonic) SL can also be used. Examples of such SL-producing yeast include *Candida magnoliae, Candida gropengisseri, Candida apicola, Candida petrophilum, Candida bogoriensis, Candida batistae*, and the like.

The culture of such SL-producing yeast in the present invention uses a culture medium containing, as carbon sources, a sugar such as glucose (hydrophilic substrate), and fatty acid, a fatty acid ester such as fatty acid triglyceride, or oil and fat such as vegetable oil containing fatty acid as a component (hydrophobic substrate). Other components of the culture medium are not particularly limited and can be suitably selected from medium components generally used for yeast.

The acidic SL-containing composition, which is the target of the present invention, refers to a composition in which acidic SL represented by formula (1) is present in a proportion of 78 mass % or more, and lactonic SL represented by formula (2) is present in a proportion of less than 22 mass %, based on the total amount of the lactonic SL and acidic SL contained in the composition taken as 100 mass %; preferably a composition in which the proportion of the acidic SL is 85 mass % or more and the proportion of the lactonic SL is less than 15 mass %; and more preferably a composition in which the proportion of the acidic SL is 90 mass % or more and the proportion of the lactonic SL is less than 10 mass %.

The ratio of acidic SL to lactonic SL in the SL-containing composition in, for example, an SL-producing yeast culture or its processed product, can be determined by the measurement method described, for example, in WO2015/020114, the contents of which are hereby incorporated by reference. Specifically, the following method can be used: a solution prepared by mixing a mixture of acidic SL and lactonic SL (SL-containing composition) with an equal volume of a 50 volume % ethanol solution is subjected to reversed-phase column chromatography as described below, and the obtained fractions are further subjected to high-performance liquid chromatography (HPLC) to quantitatively analyze the SL content of each elution fraction.

Fractionation by Reversed-Phase Column Chromatography (1) A solution obtained by mixing 600 g of an SL-containing composition and an equal volume of 50 volume % ethanol solution (sample solution) is subjected to reversed-phase column chromatography under the following conditions.

Solid phase: $C_{18}$ column (Cosmosil® 40C18-PREP, produced by Nacalai Tesque, Inc., 7.5 kg)

Size of packed column: 15 cm×90 cm

Mobile phase: an aqueous ethanol solution having an ethanol concentration of 50 to 95 volume %

(2) To the solid phase with the sample solution, 10 L of a 50% aqueous ethanol solution, 10 L of a 80% aqueous ethanol solution, 15 L of a 90% aqueous ethanol solution, and 15 L of a 95% aqueous ethanol solution are subjected sequentially, and the fractions eluted with the 80% aqueous ethanol solution, the 90% aqueous ethanol solution, and the 95% aqueous ethanol solution are each collected.

(3) Each elution fraction is evaporated to dryness and then dissolved in ethanol. These solutions are used as test samples and subjected to HPLC under the following conditions.

Quantitative Analysis by HPLC

Conditions

Device: Shimadzu Corporation LC-10 AD-VP

Column: Inertsil ODS-3 (4.6 mm×250 mm)

Column temperature: 40° C.

Mobile phase: [A] distilled water,

[B] Methanol gradient containing 0.1 volume % formic acid

Gradients: 0 min→60 min: [B] 70→100 volume %

60 min→70 min: [B] 100→70 volume %.

Flow rate: 1.0 mL/min

Sample injection volume: 10 μL

Detector: Evaporative light scattering detector (ELSD-LTII, produced by Shimadzu Corporation)

Detector temperature: 40° C.

Gain: 5

Gas pressure: 350 kpa ($N_2$ gas)

The fraction eluted with the 80% aqueous ethanol solution contains acidic SL represented by the following formula (1a) among acidic SLs represented by formula (1). Among acidic SLs represented by formula (1), this type of acidic SL is an acidic SL represented by formula (1), in which all $R_5$ are a hydrogen atom. In the HPLC under the above conditions, the acidic SL (1a) elutes in a retention time zone of 10 to 25 minutes.

(1a)

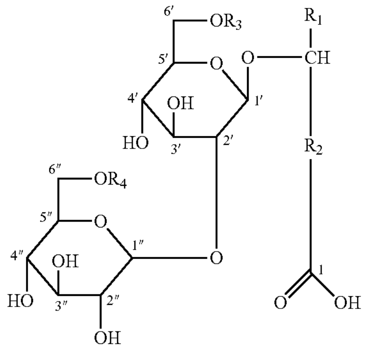

(In formula (1a), $R_1$ to $R_4$ are the same as defined in formula (1).)

The fraction eluted with the 80% ethanol aqueous solution contains not only the acidic SL (1a) but also the lactonic SL represented by formula (2) above. In the HPLC under the above conditions, the lactonic SL (2) elutes in a retention time zone of 25 to 40 minutes.

The fraction eluted with the 90% aqueous ethanol solution contains acidic SL (1b), which is one of the acidic SLs represented by formula (1) wherein one $R_5$ is a saturated or unsaturated fatty acid residue that may have a hydroxy group and the rest of the $R_5$ are a hydrogen atom. In the HPLC under the above conditions, the acidic SL (1b) elutes in a retention time zone of 45 to 60 minutes.

The fraction eluted with the 95% ethanol solution contains dimeric SL represented by formula (3). In HPLC under the above conditions, the dimeric SL (3) elutes in a retention time zone of 60 to 70 minutes.

Thus, the ratio of acidic SL to lactonic SL contained in the SL-containing composition can be determined from the area ratio of the peaks detected in each retention time zone in HPLC under the above conditions.

In the present specification, among SL-containing compositions (including liquid cultures and processed products thereof) produced by fermentation of SL-producing yeast, compositions in which the proportion of acidic SL, based on the total amount of acidic SL and lactonic SL contained in the SL-containing composition taken as 100 mass %, is 78 mass % or more, are collectively referred to as the "acidic sophorolipid-containing composition" ("acidic SL-containing composition"). On the other hand, compositions in which the proportion of acidic SL is less than 65 mass % and the lactonic SL accounts for the remaining 35 mass % or more, based on the total amount of the acidic SL and lactonic SL contained in the SL-containing composition taken as 100 mass %, are collectively referred to as the "composition containing lactonic sophorolipid and acidic sophorolipid" ("composition containing lactonic SL and acidic SL"). Since the former acidic SL-containing composition can be produced by hydrolysis of the latter composition containing lactonic SL and acidic SL, the acidic SL-containing composition produced by this method is herein referred to as a "hydrolysate of the composition containing lactonic SL and acidic SL" (which may also be referred to simply as the "hydrolysate of the present invention" or the "hydrolysate with browning resistance"). Although this is not restrictive, the browning reaction caused by lipids, polyphenols, amino acids, carbohydrates, or the like contained in the composition containing lactonic SL and acidic SL is considered to be inhibited in the acidic SL-containing composition of the present invention (the hydrolysate of the present invention).

In the present invention, the acidic SL-containing composition (hydrolysate of the present invention) can be further classified into crudely purified acidic SL-containing compositions and purified acidic SL-containing compositions according to, for example, the presence or absence of purification treatment of the acidic SL-containing composition, the degree of purification (purity of acidic SL), liquid property, degree of saponification, or proportion of acidic SL.

Crudely purified acidic SL-containing compositions as referred to herein include acidic SL-containing compositions that have not undergone any purification treatment other than solid-liquid separation, such as centrifugation or filtration, among the SL-producing yeast-processed products (most of which are hydrolysates, especially alkaline hydrolysates). In contrast, purified acidic SL-containing compositions mean acidic SL-containing compositions that have been subjected to purification treatment, such as extraction treatment with organic solvents or the like and column chromatography, regardless of the degree of purification.

(II) Acidic SL-Containing Composition (Hydrolysate of the Present Invention)

The acidic SL-containing composition of the present invention is a composition (hydrolysate) that is obtained by hydrolyzing a composition containing lactonic SL and acidic SL (including a liquid culture of SL-producing yeast and a solid-liquid separation product thereof). The acidic SL-containing composition (the hydrolysate of the present invention) is distinguished from purified acidic SL-containing compositions that are purified by a treatment such as extraction with an organic solvent or the like or column chromatography after the hydrolysis treatment in that it is a roughly purified acidic SL-containing composition that has not undergone any advanced purification treatment other than solid-liquid separation, such as centrifugation and filtration.

The hydrolysis treatment generally includes alkaline hydrolysis (saponification), acid hydrolysis, and enzymatic treatment. In the present invention, alkaline hydrolysis (saponification) is preferred.

Further, the acidic SL-containing composition of the present invention (the hydrolysate of the present invention) is different from previously known roughly purified acidic SL-containing compositions in that a filtrate of the hydrolysate of the composition containing lactonic SL and acidic SL has at least the following features (1) and (2):

(1) hue value (Abs. 440): 5 or less; and (2) ethanol-insoluble content: less than 3 mass %.

The hue value (Abs. 440) (1) reflects the degree of browning (degree of coloration) of the hydrolysate obtained by hydrolyzing the composition containing lactonic SL and acidic SL. The higher the value, the higher the degree of browning (coloration). The lower the value, the lower the degree of browning (coloration). The "filtrate of the hydrolysate of the composition containing lactonic SL and acidic SL" as referred to herein means, for example, a filtrate obtained by hydrolyzing a composition containing lactonic SL and acidic SL, which is a liquid culture of an SL-producing yeast or a solid-liquid separation product thereof, returning the obtained hydrolysate to room temperature (25±5° C.), allowing the hydrolysate to stand for 1 week, then removing the resulting insoluble matter by filtration through a filter with a pore size of 0.45 μm, and collecting the filtrate. The "filtrate of the hydrolysate of the composition containing lactonic SL and acidic SL" is a standard sample to be used as a reference for measuring and evaluating the features (2) to (6) described below as well as the hue value (Abs. 440) (1) in defining the acidic SL-containing composition of the present invention (the hydrolysate of the present invention). This is not intended to mean that the acidic SL-containing composition of the present invention (the hydrolysate of the present invention) is limited to this standard sample.

The hue value (Abs. 440) (1) can be determined as follows. The filtrate of the hydrolysate of the composition containing lactonic SL and acidic SL is dissolved in distilled water to achieve an ethanol-insoluble content of 3 mass %. The obtained diluted aqueous solution is filtered through a filter with a pore size of 0.45 μm, and the absorbance of the filtrate at a wavelength of 440 nm is measured using an infrared/UV-visible spectrophotometer. The absorbance (Abs. 440 nm) is multiplied by 10, thus obtaining the hue value. The ethanol-soluble content can be measured in accordance with JIS K 3362-2008. The details are described in the Examples section. The acidic SL-containing composition of the present invention (the hydrolysate of the present invention) is such that a filtrate of the hydrolysate of the composition containing lactonic SL and acidic SL has a hue value (Abs. 440) of preferably 2 or less, and more preferably 1.5 or less, and even more preferably 1.3 or less.

The ethanol-insoluble content (mass %) (2) refers to the amount of ethanol-insoluble matter contained in the filtrate of the hydrolysate of the composition containing lactonic SL and acidic SL. The ethanol-insoluble content can be measured in accordance with the measurement method for ethanol-insoluble content specified in JIS K 3304:2006 "Soap Testing Method." The details will be explained in the Examples section. The acidic SL-containing composition of the present invention (the hydrolysate of the present invention) is such that a filtrate of the hydrolysate of the composition containing lactonic SL and acidic SL preferably has an ethanol-insoluble content of 2 mass % or less, more preferably 1.5 mass % or less, and even more preferably 1.3 mass % or less.

The acidic SL-containing composition of the present invention (the hydrolysate of the present invention) is characterized in that a filtrate of the hydrolysate of the composition containing lactonic SL and acidic SL has, in addition to the above features (1) and (2), at least one of the following features (3) to (6):

(3) hue value (Abs. 440) after being left in the dark at 50° C. for 1 month: 10 or less;

(4) liquid property (pH): pH of 6 to 9;

(5) saponification value: 1 to 25 mgKOH/g; and (6) ignition residue: 16 mass % or less.

The acidic SL-containing composition of the present invention (the hydrolysate of the present invention) preferably has, in addition to the above features (1) and (2), feature (3) when a filtrate of the hydrolysate of the composition containing lactonic SL and acidic SL is allowed to stand for 1 month (30 days) in the dark at 50° C. As shown in this feature, the acidic SL-containing composition having feature (3) has suppressed browning for a long period of time. In this sense, in terms of excellent storage stability (browning resistance) as well, this acidic SL-containing composition can be distinguished from previously known roughly purified acidic SL-containing compositions. This feature can also be measured in accordance with the method of measuring the hue value (Abs. 440) described above. The details are explained in the Examples section. A suitable acidic SL-containing composition of the present invention (hydrolysate of the present invention) is such that after a hydrolysate of the composition containing lactonic SL and acidic SL is filtered and the obtained filtrate of the hydrolysate is allowed to stand under the above conditions, the filtrate has a hue value (Abs. 440) of 9 or less, more preferably 5 or less, even more preferably 3 or less, and particularly preferably 2 or less.

The acidic SL-containing composition of the present invention (the hydrolysate of the present invention) is more preferably such that the filtrate of the hydrolysate of the composition containing lactonic SL and acidic SL has feature (4) in addition to the above features (1) and (2) or features (1) to (3). The acidic SL-containing composition having feature (4) can maintain a relatively stable browning-suppressed state over time and even when heated, and can be provided as a roughly purified acidic SL-containing composition with low coloration or browning resistance. A suitable acidic SL-containing composition of the present invention (hydrolysate of the present invention) is such that when a hydrolysate of the composition containing lactonic SL and acidic SL is filtered, the obtained filtrate of the hydrolysate has a pH of 6 to 9, preferably a pH of 7 to 9, and more preferably a pH of 7.5 to 8.5 (pH-adjusted product). If the filtrate of the hydrolysate of the composition containing lactonic SL and acidic SL has a pH of 6 to 9 from the beginning, no adjustment is necessary. However, when the pH is not within this range or if the pH should be set to a more suitable pH range, pH adjustment can be made by adding and mixing a known pH adjustment agent into the filtrate. This can stably suppress browning (progression and increase of browning) and enables the production of a composition containing a roughly purified acidic SL with low coloration or browning resistance. Examples of pH-adjusting agents include, but are not limited to, sulfuric acid, hydrochloric acid, nitric acid, phosphoric acid, boric acid, and hydrofluoric acid; organic acids such as formic acid, acetic acid, malic acid, citric acid, oxalic acid, glutamic acid, and aspartic acid. Preferably inorganic acids such as sulfuric acid are used.

The acidic SL-containing composition of the present invention (the hydrolysate of the present invention) is more preferably such that a filtrate of the hydrolysate of the composition containing lactonic SL and acidic SL has at least one of features (5) and (6) in addition to the above features (1) and (2), features (1) to (3), or features (1) to (4). The saponification value (5) refers to the amount of free acids (fatty acids and hydroxy fatty acids) and esters (ester linkages of SL, and lactone ring of SL) contained in the filtrate after the composition containing lactonic SL and acidic SL is hydrolyzed. The smaller the value, the smaller the amount of free acids, acetyl groups of SL, and lactonic SL remaining in the acidic SL-containing composition. In other words, the smaller the value, the higher the proportion of acidic SL and the lower the cytotoxicity caused by free acids (fatty acids and hydroxy fatty acids) and acetyl groups of SL. The saponification value can be measured in accordance with the neutralization titration method for measuring the saponification value specified in JIS K 0070:1992 "Test methods for acid value, saponification value, ester value, iodine value, hydroxyl value and unsaponifiable matter of chemical products." The details are explained in the Examples section. The acidic SL-containing composition of the present invention (the hydrolysate of the present invention) is such that a filtrate of the hydrolysate of the composition containing lactonic SL and acidic SL preferably has a saponification value of 25 mgKOH/g or less, more preferably 20 mgKOH/g or less, and even more preferably 15 mgKOH/g or less. The lower limit of the value is 0, preferably 10 mgKOH/g, and more preferably 7 MgKOH/g.

The ignition residue (6) refers to the amount of inorganic compounds contained in the filtrate of the hydrolysate of the composition containing lactonic SL and acidic SL (in terms of sulfate). The lower the value, the smaller the amount of inorganic compounds contained as impurities. The ignition residue can be measured in accordance with "Ignition Residue Test Method 4" specified in JIS K 0067:1992 JIS K 0067-1992 "Test Methods for Loss and Residue of Chemical Products." The details are described in the Examples section. The acidic SL-containing composition of the present invention (the hydrolysate of the present invention) is such that a filtrate of the hydrolysate of the composition containing lactonic SL and acidic SL preferably has an ignition residue of 16 mass % or less, more preferably 13 mass % or less, and even more preferably 11 mass % or less. The amount of ignition residue is preferably small because it can cause precipitation and makes emulsion unstable in emulsion formulation. The lower limit is 0 and is preferably, for example, 1.5 mass %, and more preferably 1.3 mass %.

The acidic SL-containing composition of the present invention (the hydrolysate of the present invention) is not particularly limited in form and may be in the form of a liquid, an emulsion, or a solid. Examples of the solid form include dry solids such as lyophilizate, spray-dried products, and evaporated dried products; and tablets, pills, powders, granules, and capsules.

(III) Use of the Acidic SL-Containing Composition (Hydrolysate of the Present Invention)

The acidic SL-containing composition (hydrolysate of the present invention) having the features described above can be used as a low-coloring or browning-resistant anionic surfactant in its original state or after any treatment as described below. The acidic SL-containing composition can also be used as an additive in foods and drinks, pharmaceuticals, quasi-drugs, perfumery and cosmetics, and detergents. When the acidic SL-containing composition is so used, purification treatments (e.g., solid-liquid separation such as filtration, solvent extraction, adsorption, and chromatography) can be further performed, if necessary, to remove impurities and reduce coloration and/or toxicity. In addition, any treatment such as pH adjustment or addition of a preservative, an antioxidant, or a storage stabilizer may be performed as long as the effect of the invention is not hindered.

The phrase "foods and drinks" as used herein includes, in addition to general food products and beverages, foods and drinks that have specific functions and are consumed, for example, for maintaining health, such as health supplements, functional health food products, food for specified health use, and supplements. The phrase "perfumery and cosmetics" as used herein includes the concepts of cosmetics and fragrance products, such as scented water, cologne, and perfume. Cosmetics refer to those applied to the body by rubbing, spraying, or other methods (e.g., pasting) similar to those for purposes such as cleaning, beautifying, and increasing the attractiveness of a person's body to change one's physical appearance, or maintaining the health of the skin or hair; and examples of cosmetics include make-up cosmetics (foundation, lipstick, etc.), basic cosmetics (face lotion, milky lotion, etc.), hair-care products (hair tonic, hair lotion, hair cream, etc.), and toiletry products (toothpaste, shampoo, hair rinse, soap, facial wash, bath fragrance, etc.). Cleaning agents are those used on a daily basis, whether they are used for commercial or domestic purposes. Cleaning agents include cleaning agents for hands, feet, and body (including for animals and humans), clothes, dishes, furniture, water areas (sinks, basins, bathrooms, toilets, etc.), and microwave ovens (including those for grease).

The acidic SL-containing composition of the present invention (hydrolysate of the present invention) having feature (5) has low cytotoxicity and low irritation in addition to browning resistance, and can therefore be suitably used as compositions for external application for which low irritation (or no irritation) is required. Specific examples of such external compositions include perfumery and cosmetics for hypersensitive skin (cosmetics and fragrance products); externally applied drug products or quasi-drugs applied to the skin with a wound or inflammation; drugs or quasi-drugs applied to the mucosa of the eyes, nasal cavity, oral cavity, or the like (e.g., nasal sprays, eye drops, ophthalmic ointments, eye lotions, nose washes, contact lens fitting liquids, and like eye-care products); and the like.

The acidic SL-containing composition of the present invention (the hydrolysate of the present invention) can be used as an anionic surfactant as described above, either as it is or after any treatment is further performed as necessary. As long as the surfactant effect is provided and the features of the present invention, such as low coloration, and preferably browning resistance as well, are not impaired, a third component for use in the preparation (formulation) of anionic surfactants may be added. Examples of such third components include, but are not limited to, solvents such as distilled water, ion exchange water, and ethanol; additives such as sodium chloride and potassium chloride; solubilizers such as glycerin, propylene glycol, and hexylene glycol; thickeners such as xanthan gum, alginate, and dextran; pH adjusters such as hydrochloric acid, sulfuric acid, boric acid, sodium hydroxide, and potassium hydroxide; chelating agents such as phosphoric acid compounds, nitrilotriacetic acid (NTA), and ethylenediaminetetraacetic acid (EDTA); and other components such as dyes, preservatives, storage stabilizers, and enzymes. When a third component is used, the amount of the acidic SL-containing composition of the present invention (the hydrolysate of the present invention) contained in the formulation of the anionic surfactant is not limited as long as it produces a surfactant effect. The amount of the acidic SL-containing composition of the present invention can be, for example, 0.005 to 99.9 mass %, preferably 0.01 to 50 mass %, more preferably 1 to 50 mass %, and particularly preferably 5 to 50 mass %, in terms of the amount of the acidic SL.

The acidic SL-containing composition of the present invention (the hydrolysate of the present invention) can be used as an additive for foods and drinks, pharmaceuticals, quasi-drugs, detergent additives, or perfumery and cosmetics (food additives, pharmaceutical additives, quasi-drug additives, detergent additives, perfumery or cosmetic additives), as described above, as is, or after being subjected to any further treatment as necessary. In this case, as long as the desired surfactant effect is achieved and the features of the present invention, such as low coloration and preferably also browning resistance, are not impaired, a third component for use in the preparation (formulation) of each of the above additives may be added. Such a third component may be set in a customary manner according to the target product, such as foods and drinks, pharmaceuticals, quasi-drugs, detergents, or perfumery and cosmetics. When the third component is mixed in, the amount of the acidic SL-containing composition of the present invention (the hydrolysate of the present invention) contained in the additive is not limited as long as it produces the desired surfactant effect. The amount of the acidic SL-containing composition of the present invention can be, for example, 0.005 to 99.9 mass %, preferably 0.01 to 50 mass %, more preferably 0.02 to 10 mass %, and particularly preferably 0.1 to 5 mass %, in terms of the amount of acidic SL.

When the acidic SL-containing composition (hydrolysate) of the present invention as is or after being further subjected to an optional treatment as necessary is used by addition in the manufacture of foods and drinks, pharmaceuticals, quasi-drugs, detergents, or perfumery and cosmetics, that is, when the acidic SL-containing composition of the present invention (hydrolysate of the present invention) is used to produce foods and drinks, pharmaceuticals quasi-drugs, detergents, or perfumery and cosmetics, the amount of the acidic SL-containing composition of the present invention (the hydrolysate of the present invention) is suitably set in accordance with the purpose and properties of each product, within the range in which the desired surfactant effect is provided. In the production, a third component usually used in the production of foods and drinks, pharmaceuticals, quasi-drugs, detergents, or perfumery and cosmetics can be added. Although this is not limitative, the acidic SL-containing composition of the present invention (the hydrolysate of the present invention) can be used, for example, in such a proportion that when added to foods and drinks, pharmaceuticals, quasi-drugs, detergents, or perfumery and cosmetics, the CMC of these products is 300 ppm or more. For example, the proportion can be, for example, 0.005 to 99.9 mass %, preferably 0.01 to 50 mass %, more preferably 0.02 to 10 mass %, and particularly preferably 0.1 to 5 mass %, in terms of the amount of the acidic SL contained in these products.

(IV) Method for Producing Acidic SL-Containing Composition (IV-1) Preparation of Starting Material (Composition Containing Lactonic SL and Acidic SL or a Processed Product Thereof)

The composition containing lactonic SL and acidic SL to be used as a starting material for producing the acidic SL-containing composition of the present invention (hydrolysate of the present invention) can be, for example, a culture of yeast that produces lactonic SL and acidic SL ("SL-producing yeast") or a processed product thereof. Examples of yeast that produces lactonic SL and acidic SL include known yeast, and preferable examples include *Candida bombicola* and the like.

A preferable method for culturing SL-producing yeast is, for example, a method of culturing the yeast by simultaneously giving a high concentration of sugar and a hydrophobic oily substrate. The method is not limited to this method. As long as the effect of the present invention is not hindered, a wide variety of methods known in the art (such as those described in JP2002-045195A, WO2013/129667, WO2015/034007, and WO2015/020114) can be used. More specifically, a method of culturing SL-producing yeast by using glucose as a sugar and using a carbon source containing fatty acid and vegetable oil as a hydrophobic oily substrate can be used.

The medium composition is not particularly limited. The fatty acid moiety of SLs is known to depend on the fatty acid chain length and proportion of the hydrophobic substrate added as a medium component, and thus can be controlled to some extent. For example, oleic acid or a lipid containing oleic acid in a high proportion is suitable for use as the hydrophobic substrate. Examples include vegetable oils such as palm oil, rice bran oil, rapeseed oil, olive oil, and safflower oil; and animal oils such lard and beef fat. For fermentative production of SLs with a stably high yield, a mixture of hydrophilic sugar and hydrophobic fat/oil is preferable as a carbon source. Glucose is frequently used as a hydrophilic substrate.

After the liquid components are separated and removed from the obtained culture by using a known solid-liquid separation method, such as centrifugal separation or decantation, the resulting solids are washed with water to obtain an SL-containing fraction (SL-containing culture). The SL-containing fraction (SL-containing culture) obtained by culturing an SL-producing yeast is a mixture of lactonic SL and acidic SL (a composition containing lactonic SL and acidic SL). The acidic SL content is less than 65 mass % (on a solids basis) based on the total amount of lactonic SL and acidic SL.

The method for recovering the composition containing lactonic SL and acidic SL from the culture of SL-producing yeast can be known methods, such as the methods described in JP2003-9896A or other publications. Such a method controls the solubility of SL in water by adjusting the pH of the SL-producing yeast culture or the SL-containing fraction prepared from the culture. Specifically, for example, the culture of SL-producing yeast is adjusted to a pH of about 6 to 7 with, for example, a NaOH solution to solubilize the SL, and then centrifuged to collect a supernatant. Subsequently, a sulfuric acid solution or the like is added to the supernatant to adjust the supernatant to a pH of about 2 to 3 to insolubilize SL. The resulting mixture is allowed to stand and then decanted to obtain a composition containing lactonic SL and acidic SL with a water content of about 50%.

(IV-2) Preparation of Acidic SL-Containing Composition

In general, the acidic SL-containing composition can be prepared by removing lactonic SL from the composition containing lactonic SL and acidic SL described above to reduce the lactonic SL. The composition containing lactonic SL and acidic SL used as a starting material may be prepared by the using the above methods by themselves or through a third party, or may be a commercially available product. Such starting materials are commercially available, for example, from Evonik Industries AG (Germany) and Wheatoleo (France).

The acidic SL-containing composition (the hydrolysate of the present invention) can be prepared by subjecting the composition containing lactonic SL and acidic SL to the hydrolysis treatment described below. According to this hydrolysis method, lactonic SL can be effectively removed from the composition containing lactonic SL and acidic SL to thereby obtain an acidic SL-containing composition that contains acidic SL in a desired proportion of 78 mass % or more per 100 mass % of the total amount of lactonic SL and acidic SL and that has suppressed browning. According to this method, the desired acidic SL-containing composition from which lactonic SL is removed and that has suppressed browning can be obtained by subjecting the composition to a saponification treatment (alkaline hydrolysis) without the necessity of combining purification treatments, such as solvent extraction treatment, adsorption treatment, and chromatography. However, this description is not intended to restrict performing any treatment, including purification treatment, in addition to the hydrolysis treatment of the present invention.

The hydrolysis treatment used in the present invention is characterized by subjecting the target composition containing lactonic SL and acidic SL to hydrolysis using 0.8 to 1.5 g eq. of an alkaline agent relative to the saponification value (mgKOH/g) of the composition under the temperature conditions of 80° C. or less.

The saponification value of the composition containing lactonic SL and acidic SL represents the amount of free acids (fatty acids and hydroxy fatty acids) and esters (ester linkages of lactone rings of SL, and acetyl groups of SL) contained. The saponification value can be measured in accordance with the neutralization titration method for measuring the saponification value specified in JIS K 0070:1992 "Test methods for acid value, saponification value, ester value, iodine value, hydroxyl value and unsaponifiable matter of chemical products." For details, refer to the description in the Examples section.

From the obtained saponification value (mgKOH/g), the amount of alkaline agent equivalent to 1 gram of the saponification value is calculated. For example, the amount of alkaline agent equivalent to 1 gram of the saponification value of the composition containing ketonic SL and acidic SL, which is used as a starting material, can be calculated according to the following formula.

$$\text{Amount of alkaline agent corresponding to 1 g eq. (g)} = S \times \text{saponification value} \times (B/C)/1000 \qquad \text{Formula 1}$$

S: Mass (g) of the composition containing ketonic SL and acidic SL, which is used as starting material B: Molecular weight of alkaline agent (e.g., 40 in the case of NaOH)

C: Molecular weight of potassium hydroxide (56.11)

The proportion of the alkaline agent required for hydrolyzing the composition containing lactonic SL and acidic SL to prepare the acidic SL-containing composition of the present invention (the hydrolysate of the present invention) is 0.8 to 1.5 g eq. to the saponification value of the composition containing lactonic SL and acidic SL. The proportion of the alkaline agent required for hydrolyzing the composition containing lactonic SL and acidic SL can be calculated by multiplying the amount of alkaline agent (g) obtained by the above formula by 0.8 to 1.5. The proportion of the alkaline agent is preferably 0.8 to 1.2 g eq., more preferably 0.8 to 1.1 g eq., even more preferably 0.9 to 1.1 g eq., and particularly preferably 1 g eq.

The alkaline agent used in the hydrolysis treatment is not limited, but can include metal salts of hydroxides (such as sodium, potassium, calcium and magnesium), carbonates, phosphates, or bases such as alkanolamines. Preferably, it is a metal salt of hydroxide, more preferably sodium hydroxide. The alkali agent is preferably a metal salt of hydroxide, and more preferably sodium hydroxide.

The temperature, pressure, and time for the hydrolysis treatment are not particularly limited as long as the purpose and effect of ring opening of lactone ring of the lactonic SL contained in the composition containing lactonic SL and acidic SL can be achieved while browning is suppressed. The temperature, pressure, and time are preferably such that the ring opening of lactone ring can proceed efficiently while suppressing side reactions (including the formation of pigment components) such as decomposition and chemical modification of the target acidic SL. The reaction temperature can be appropriately adjusted in accordance with the amount of alkali agent used within the range of 80° C. or less, and preferably 20 to 80° C. For example, when an alkaline agent is used in an amount of 0.8 to 0.9 g eq. to the saponification value of the composition containing lactonic SL and acidic SL, the temperature can be within the range of 80° C. or less, preferably 20 to 80° C., and more preferably 30 to 80° C. When an alkaline agent is used in an amount of 0.9 to 1 g eq. relative to the saponification value of the composition containing lactonic SL and acidic SL, the temperature is preferably within the range of 20 to 60° C., more preferably 25 to 50° C. Further, when an alkaline agent is used in an amount of 1 to 1.2 g eq. relative to the saponification value of the composition containing lactonic SL and acidic SL, the temperature is preferably within the range of 20 to 50° C., and more preferably 25 to 40° C. When an alkaline agent is used in an amount of 1.2 to 1.5 g eq. relative to the saponification value of the composition containing lactonic SL and acidic SL, the temperature is preferably within the range of 20 to 50° C., and more preferably 25 to 35° C.

The pressure, although not limited, can usually be selected from the range of 1 atm to 10 atm, preferably 1 atm to 2 atm, and particularly preferably 1 atm (atmospheric pressure). The reaction time is usually in the range of 10 minutes to 5 hours, and preferably about 1 hour to about 3 hours.

The acidic SL-containing composition of the present invention (the hydrolysate of the present invention) can be prepared by such hydrolysis treatment. The acidic SL-containing composition of the present invention (the hydrolysate of the present invention) can also be prepared by further adjusting the hydrolysate obtained by the above treatment to room temperature (25±5° C.) and filtering off the insoluble matter produced in the process. Further, the acidic SL-containing composition (the hydrolysate of the invention) can also be prepared by adjusting the hydrolysate to room temperature (25±5° C.), then adjusting the hydrolysate to a pH of 6 to 9, and filtering off the insoluble matter produced in the process. The order of adjustment to room temperature and pH adjustment is not limited to this order, and the hydrolysate can be adjusted to room temperature after the pH adjustment. By adjusting the pH of the hydrolysate to the range of a pH of 6 to 9, the progress of coloration over time can be suppressed, and a browning-resistant acidic SL-containing composition with good storage stability can be prepared. Preferred pH conditions are a pH of 7 to 9, more preferably the range of a pH of 7.5 to 8.5.

An acidic SL-containing composition whose filtrate after hydrolysis (filtrate of the hydrolysate) has the above features (1) to (2) can be thus prepared. The "filtrate after hydrolysis" ("filtrate of the hydrolysate") as referred to herein means a filtrate obtained by, after the adjustment to room temperature or pH adjustment, filtering off the insoluble matter produced in the hydrolysate using a filter with a pore diameter of 0.45 μm and collecting the filtrate. The acidic SL-containing composition of the present invention (the hydrolysate of the present invention) preferably has feature (3) in addition to features (1) to (2), and more preferably has the above feature (4) in addition to features (1) to (2) or features (1) to (3). According to the above production method, an acidic SL-containing composition having the above feature (5) and/or (6) in addition to features (1) to (2), features (1) to (3), features (1) to (2) and (4), or features (1) to (4) can be prepared. Features (1) to (6) and their measurement methods are as described above, the description details of which are hereby incorporated by reference in their entirety.

(V) Hydrolysis Method for Producing Acidic SL-Containing Composition with Browning Resistance (Hydrolysate with Browning Resistance)

The present invention also provides a hydrolysis method for producing an acidic SL-containing composition with browning resistance (hydrolysate with browning resistance). The present invention also provides a method for inhibiting browning of an acidic SL-containing composition. The method can be carried out by subjecting the composition containing lactonic SL and acidic SL to step (a):

step (a): reacting a composition containing lactonic SL and acidic SL under conditions of 80° C. or less using an alkaline agent in an amount of 0.8 to 1.5 g eq. based on the saponification value of the composition containing lactonic SL and acidic SL.

According to this method, an acidic SL-containing composition whose filtrate after hydrolysis has at least the following features (1) and (2) can be obtained:

(1) hue value (Abs. 440): 5 or less; and (2) ethanol-insoluble content: less than 3 mass %.

According to this method, an acidic SL-containing composition that has at least one of the following features (3) to (6) in addition to the above features (1) and (2) can be produced.

The method of the present invention may further comprise the following step (b) after the above step (a): step (b): adjusting the hydrolysate obtained in step (a) or a filtrate of the hydrolysate to a pH of 6 to 9.

A browning-resistant acidic SL-containing composition with stable suppression of coloration over time (hydrolysate with browning resistance) can be thus prepared.

Each step in the hydrolysis method of the present invention, the starting material used (composition containing lactonic SL and acidic SL), the obtained acidic SL-containing composition with browning resistance (hydrolysate with browning-resistance), their features, evaluation methods therefor, etc. are as described above in (I) through (IV), and the descriptions for each are incorporated herein by reference.

The terms "containing" and "comprising" as used herein include the meanings of consisting essentially of and consisting of.

EXAMPLES

In order to aid understanding of the structure and effect of the present invention, the present invention is described below with reference to experimental examples. However, the present invention is not limited to these experimental examples (Examples and Comparative Examples). Various modifications are possible within the spirit of the present invention by a person skilled in the art. Unless otherwise specified, the following experiments were conducted at room temperature (25±5° C.) and atmospheric pressure conditions.

Various physical properties (hue value (Abs. 440), ethanol-soluble content, ethanol-insoluble content, saponification value, and ignition residue) of the acidic SL-containing compositions prepared in Production Examples 1 and 2 described below were determined according to the following methods.

(a) Hue Value of Filtrate of Hydrolysate (Abs. 440)

The filtrate after hydrolysis of the composition containing lactonic SL and acidic SLs is placed in a measuring flask and diluted with distilled water to achieve an ethanol-soluble content of 3 mass %. The obtained diluted aqueous solution is promptly filtered through a filter with a pore size of 0.45 μm to collect the filtrate, and the absorbance of the obtained filtrate is measured at a wavelength of 440 nm using an infrared/UV-visible spectrophotometer. The absorbance of the filtrate obtained (Abs. 440 nm) is multiplied by 10, and the obtained value is defined as a hue value of the filtrate after hydrolysis of the composition (Abs. 440). The ethanol-soluble content of the filtrate can be determined by the method described in (c) below.

(b) Hue Value of the Filtrate of the Hydrolysate after being Allowed to Stand at 50° C. for 1 Month (Abs. 440)

The filtrate after hydrolysis of the composition containing lactonic SL and acidic SL is placed in a light-shielded incubator of 50° C. for 1 month (30 days), and then transferred to a measuring flask. The filtrate is diluted with distilled water to achieve an ethanol-soluble content of 10 mass %. The obtained diluted aqueous solution is filtered through a filter with a pore size of 0.45 μm to collect the filtrate. The absorbance of the filtrate at a wavelength of 440 nm is measured using an infrared/UV-visible spectrophotometer. The absorbance of the filtrate obtained (Abs. 440 nm) is multiplied by 10, and the obtained value is defined as a hue value (Abs. 440) of the filtrate of the hydrolysate of the titled compound after being allowed to stand at 50° C. for 1 month. The ethanol-soluble content of the filtrate can be determined by the method described in (c) below.

(c) Ethanol-Soluble Content

The ethanol-soluble content refers to the amount of substance dissolved in ethanol when the test sample dissolved in ethanol, and can be measured in accordance with the provisions of JIS K3362-2008.

Measuring Method

An Erlenmeyer flask and a glass filter are accurately weighed. The weights of these instruments are measured after being dried at 105° C. for at least 2 hours and allowed to cool in a desiccator. About 5 g of the test sample (filtrate of the hydrolysate or filtrate after being allowed to stand at 50° C. for 1 month) is accurately weighed out to one milligram and placed into the Erlenmeyer flask. After 100 mL of ethanol is added to the test sample, the flask is equipped with a glass tube and heated in a water bath for 30 minutes while occasionally shaking for dissolution. For liquid or paste samples, 99.5 vol % ethanol is used. After the warm solution is filtered as is through a glass filter, 50 mL of ethanol is added to the residue in the Erlenmeyer flask again to dissolve the residue. The resulting warm solution is filtered using a glass filter, and the Erlenmeyer flask and the glass filter are washed well with hot ethanol. After being allowed to cool to room temperature, the filtrate and the wash are transferred to a 250-mL volumetric flask, and ethanol is added to a marked line. Using a transfer pipette, 100-mL portions of the liquid are aliquoted into two 200-mL beakers with a known mass. After one of the beakers is heated in a water bath to remove ethanol, the residue is dried for 1 hour in a dryer adjusted to 105±2° C. and allowed to cool in a desiccator, and the dry residue (g) is then accurately weighed.

Calculation method for ethanol-soluble content — Formula 2

$$\text{Ethanol-soluble content (mass \%)} = (A/[S\times 100/250])\times 100 = ([250\times A]/S)$$

$A$: Amount (g) of the dry residue (g)

$S$: Mass (g) of the test sample (g)

(d) Ethanol-Insoluble Content (Mass %)

The ethanol-insoluble content refers to the amount of insoluble matter obtained by dissolving the test sample in 99.5 vol % ethanol (99.5) and filtering the solution. The ethanol-insoluble matter is measured by the following method in accordance with the ethanol-insoluble content specified in JIS K 3304: 2006 "Soap Test Method."

Measuring Method (a) About 5 g of the test sample (filtrate after hydrolysis) is placed in a 500-mL Erlenmeyer flask and weighed to a precision of 1 mg (S: mass of the test sample). 200 mL of ethanol (95) is added thereto and a reflux cooler is attached to heat and dissolve the test sample in a water bath.

(b) This solution is filtered through filter paper or a glass filter. The filter paper or glass filter to be used is dried beforehand in a dryer adjusted to 105±2° C., cooled, and then weighed for mass.

(c) The insoluble matter remaining in the Erlenmeyer flask is washed two or three times with a small amount of ethanol (95) heated to near boiling point and completely transferred to the filter paper or glass filter.

(d) Further, the insoluble matter is washed well with warm ethanol (95) and filtered.

(e) The filter paper or glass filter through which the ethanol-insoluble matter is filtered is dried for 1 hour with a dryer adjusted to 105±2° C., then allowed to cool in a desiccator and weighed for mass.

(f) The procedures of (e) are repeated until the difference between two successively measured weights is 1 mg or less.

(g) The obtained mass is divided by the mass of the filter paper or glass filter that has been measured beforehand to obtain the mass of the ethanol-insoluble matter (A).

Calculation Method for Ethanol-Insoluble Matter $$\text{Ethanol-insoluble matter (mass \%)}=(A/S)\times 100 \quad \text{Formula 3}$$

S: Mass of the sample (g)

A: Mass of ethanol-insoluble matter (g)

(e) Saponification Value (mgKOH/g)

The saponification value refers to the amount in terms of mg of potassium hydroxide required to neutralize free acids (fatty acids and hydroxy fatty acids) and to saponify esters (ester linkages of lactonic SL and acetyl groups of SL) in 1 g of a test sample. The saponification value is determined by the following method in accordance with the neutralization titration method specified in JIS K 0070:1992 "Test methods for acid value, saponification value, ester value, iodine value, hydroxyl value and unsaponifiable matter of chemical products."

Measuring Method (a) 1.5 to 2.0 g of the test sample (filtrate after hydrolysis) is weighed to a precision of 1 mg in a 200-mL to 300-mL Erlenmeyer flask (S: mass of the test sample). The amount of the test sample to be collected is such an amount that the volume of 0.5 mol/L hydrochloric acid needed to titrate the sample is approximately half the volume required for the empty test.

(b) 25 mL of a 0.5 mol/L potassium hydroxide ethanol solution is added to the sample by using a transfer pipette. The 0.5 mol/L potassium hydroxide ethanol solution can be prepared by dissolving 35 g of potassium hydroxide in 20 mL of water, adding ethanol (95) to make 1 L, allowing the resulting mixture to stand for 2 to 3 days while blocking carbon dioxide, and then performing filtration.

(c) An air cooler is attached to the Erlenmeyer flask. While occasionally shaking and mixing the content, the content is gently heated in a water bath, a sand bath, or on a hot plate to react for 30 minutes.

(d) Immediately after the reaction is completed, cooling is performed. Before the content has hardened into an agar-like state, the inner wall is washed while spraying a small amount of water from the top of the air cooler. The air cooler is then removed.

(e) 1 mL of a phenolphthalein solution (10 g/L) is added as an indicator, and titration is performed with 0.5 mol/L hydrochloric acid. The end point of the reaction is defined as the time when for about 1 minute the light red color of the indicator no longer appears (C: titer of the test sample).

(f) For the empty test, steps (a) through (e) are performed without using any test samples, and the titer (B) in the empty test is determined.

Calculation Method for Saponification Value $$\text{Saponification value}=([B-C])\times f\times 28.05)/S \quad \text{Formula 4}$$

B: Amount of 0.5 mol/L hydrochloric acid used for titration in the empty test (mL)

C: Amount of 0.5 mol/L hydrochloric acid used for titration of the test sample (mL)

f: 0.5 mol/L hydrochloric acid factor

S: Mass of the test sample (g)

28.05: Number of milligrams of potassium hydroxide in an amount equivalent to the amount of hydrochloric acid contained in 1 mL of 0.5 mol/L hydrochloric acid (mg/mL)

(f) Ignition Residue (Mass %)

The ignition residue refers to the percentage of inorganic compounds contained in the test sample (in terms of sulfates). The ignition residue is measured by the following method in accordance with method 4 for ignition residue test methods specified in JIS K 0067:1992 "Test Methods for Loss and Residue of Chemical Products."

Measurement Method (a) Each sample is weighed to a precision of 0.1 mg in a crucible or an evaporating dish having a constant weight.

(b) About 0.2 ml of sulfuric acid is added to the crucible or evaporating dish containing the sample, and the sample is gradually heated on a hot plate without boiling to evaporate or carbonize the sample, and the heating is continued until white smoke is no longer produced.

(c) Subsequently, the crucible containing the ashen sample is placed in an electric furnace and heated intensely at 500±50° C. for 1 hour.

(d) The crucible removed from the electric furnace is promptly transferred to a desiccator and allowed to cool and then removed from the desiccator. The mass is weighed to a precision of 0.1 mg (measured value (residue)).

(e) Steps (c) and (d) are repeated until a constant amount is achieved.

(f) The ignition residue (%) is calculated from the measured value (residue) and the collected amount measured in advance according to the following formula.

Calculation Method for Ignition Residue $$\text{Ignition residue (sulfate) (mass \%)}=(W2-W3)/[W1-W3])\times 100$$

W1: Mass of the test sample and crucible before ignition (sampled amount) (g)

W2: Mass of the test sample and crucible after ignition (measured amount) (g)

W3: Mass of crucible (g)

Reference Production Example 1: Extraction of Sophorolipid (Preparation of Composition Containing Lactonic SL and Acidic SL)

A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of a yeast extract (produced by Asahi Food & Healthcare Co., Ltd., product name: Meast Powder N) was used as a culture medium. *Candida bombicola* ATCC22214 was cultured in the medium while being shaken at 30° C. for 2 days. This was used as a liquid pre-culture.

The liquid pre-culture was inoculated in a proportion of 4% into a main culture medium (3 L) placed in a 5-liter fermenter, and then cultured at 30° C. at an aeration rate of 0.6 vvm for 6 days for fermentation. The main culture medium contained, per liter, 100 g of aqueous glucose, 50 g of palm olein (produced by NOF Corporation, product name: Palmary 2000), 50 g of oleic acid (produced by Acid Chem, product name: Palmac 760), 1 g of sodium chloride, 10 g of monopotassium phosphate, 10 g of magnesium sulfate heptahydrate, 2.5 g of yeast extract (produced by Asahi Food & Healthcare Co., Ltd., product name: Meast Powder N), and 1 g of urea (pH of 4.5 to 4.8 before sterilization).

On the sixth day from the start of culturing, the fermentation was stopped. The liquid culture removed from the fermenter was heated and then returned to room temperature and allowed to stand for 2 to 3 days. As a result, the liquid culture was separated into the following three layers in this order from the bottom: a liquid brown precipitate layer, a milky-white solid layer presumably mainly containing fungal cells, and a supernatant. After the supernatant was removed, industrial water or groundwater was added in an amount equal to the amount of the supernatant removed. While the resulting mixture was stirred, a 48 mass % aqueous sodium hydroxide solution was gradually added to adjust the mixture to a pH of 6.5 to 6.9, thus solubilizing SLs contained in the liquid culture. The resulting product was centrifuged with a tabletop centrifuge (Westfalia, produced by Westfalia Separator AG) to precipitate milky-white solids, and a supernatant was collected. While the collected supernatant was stirred, an aqueous 62.5 mass % sulfuric acid solution was gradually added to adjust the supernatent to a pH of 2.5 to 3.0, thus insolubilizing SLs again. After the resulting mixture was allowed to stand for 2 days, the supernatant was as much as possible removed by decantation. The residue was obtained as a crudely purified SL-containing composition (having a water content of about 50%, Reference Example 1). The composition containing lactonic SL and acidic SL contains less than 65 mass % of acidic SL and 35 mass % or more of lactonic SL.

Production Example 1: Preparation of Crudely Purified Acidic SL-Containing Composition (No. 1)

The saponification value of the composition containing lactonic SL and acidic SL obtained above in Reference Production Example 1 was measured. A 48 mass % aqueous sodium hydroxide solution was added in an amount to achieve an alkali equivalent relative to the saponification value as shown in Tables 1 to 3, and treatment was performed for 2 hours at a temperature shown in Tables 1 to 3 for 2 hours for alkali hydrolysis (saponification). After the reaction, the hydrolysate was returned to room temperature (25° C.) and allowed to stand for 1 week. The insoluble matter produced was then removed by filtration using a filter with a pore diameter of 0.45 μm. The collected filtrate (filtrate of the hydrolysate) was obtained as a crudely purified acidic SL-containing composition (Examples 1 to 13 and Comparative Examples 1 to 11). The crudely purified acidic SL-containing composition contains 78 mass % or more of the acidic SL and less than 22 mass % of the lactonic SL, based on the total of the acidic SL and lactonic SL defined as 100 mass %.

Using the filtrate of the collected hydrolysate (crudely purified acidic SL-containing composition) as a test sample, various physical properties (pH, hue value (Abs. 440), ethanol-insoluble content (mass %), saponification value (mgKOH/g), and ignition residue (mass %)) were measured by the methods described above. The filtrate after hydrolysis was further allowed to stand in the dark at 50° C. for 1 month (30 days). The hue value (Abs. 440) was then measured by the method described above. Tables 1 to 3 show the results.

Tables 1 to 3 also show the results of evaluation performed based on the following criteria.

Evaluation Criteria

+++: The hue value (Abs. 440) of the filtrate of the hydrolysate is 1.5 or less, and the hue value (Abs. 440) after 1 month at 50° C. is 1.7 or less.

++: The hue value (Abs. 440) of the filtrate of the hydrolysate is 2 or less, and the hue value Abs. 440) after 1 month at 50° C. is more than 1.7 and 3 or less.

+: The hue value (Abs. 440) of the filtrate of the hydrolysate is 5 or less, and the hue value (Abs. 440) after 1 month at 50° C. is more than 3 and 10 or less.

−: The hue value (Abs. 440) of the filtrate of the hydrolysate is more than 5, or the hue value (Abs. 440) after 1 month at 50° C. is more than 10.

TABLE 1

| | Examples | | | | | | | | | |
|---|---|---|---|---|---|---|---|---|---|---|
| | 1 | 2 | 3 | 4 | 5 | 6 | 7 | 8 | 9 | 10 |
| Alkali equivalent (g eq.) | | | 0.8 | | | | | 1.0 | | |
| Temperature (° C.) | 40 | 50 | 60 | 70 | 80 | 25 | 30 | 40 | 50 | 60 |
| pH (25° C.)* | 8.42 | 8.4 | 8.3 | 8.3 | 8.1 | 12.44 | 12.1 | 11.21 | 12.4 | 12.3 |
| (1) Hue value (Abs. 440) | 0.90 | 0.91 | 0.93 | 0.97 | 0.95 | 1.10 | 1.00 | 1.10 | 1.11 | 121 |
| Ethanol-insoluble content (mass %) | 0.8 | 0.7 | 0.8 | 0.8 | 0.7 | 1.0 | 1.1 | 1.0 | 1.0 | 1.2 |
| Saponification value (mgKOH/g) | 15.87 | 15.37 | 15.11 | 13.14 | 13.74 | 4.99 | 438 | 2.71 | 3.10 | 2.88 |
| Ignition residue (mass %) | 8.4 | 8.1 | 8.1 | 8.5 | 8.4 | 9.9 | 10.4 | 10.1 | 10.5 | 10.1 |
| (2) Hue value after being allowed to stand at 50° C. for 1 month (Abs. 440) | 1.2 | 1.2 | 1.2 | 1.3 | 1.4 | 1.77 | 2.11 | 2.02 | 2.8 | 8.2 |
| Evaluation | +++ | +++ | +++ | +++ | +++ | ++ | ++ | ++ | ++ | + |

*Glass electrode method (the same applies below)

(1) Hue value of the filtrate after hydrolysis (Abs. 440 nm)

(2) Hue value of the filtrate after being allowed to stand at 50° C. for 1 month (Abs. 440 nm) (the same applies below).

TABLE 2

| | Example | | | Comparative Example | | | | | | |
|---|---|---|---|---|---|---|---|---|---|---|
| | 11 | 12 | 13 | 1 | 2 | 3 | 4 | 5 | 6 | 7 |
| Alkali equivalent (g eq.) | 1.2 | 1.5 | | 1.0 | | 1.5 | | | 2.0 | |
| Temperature (° C.) | 40 | 40 | 50 | 70 | 80 | 70 | 80 | 25 | 50 | 60 |
| pH (25° C.)* | 12.8 | 12.55 | 12.9 | 12.1 | 12.1 | 12.7 | 12.6 | 13< | 13< | 13< |
| (1) Hue value (Abs. 440) | 1.14 | 1.10 | 1.10 | 7.77 | 8.20 | 12.13 | 15< | 1.25 | 1.10 | 11.99 |
| Ethanol-insoluble content (mass %) | 1.8 | 2.6 | 2.7 | 1.1 | 1.2 | 2.5 | 2.6 | 9.3 | 9.4 | 9.4 |
| Saponification value (mgKOH/g) | 3.42 | 2.43 | 2.38 | 1.95 | 1.81 | 2.01 | 1.90 | 2.22 | 1.93 | 1.81 |
| Ignition residue (mass %) | 15.1 | 15.5 | 14.9 | 10.4 | 10.5 | 15.3 | 15.3 | 18.7 | 19.1 | 19.2 |

TABLE 2-continued

| | Example | | | Comparative Example | | | | | | |
|---|---|---|---|---|---|---|---|---|---|---|
| | 11 | 12 | 13 | 1 | 2 | 3 | 4 | 5 | 6 | 7 |
| (2) Hue value after being allowed to stand at 50° C. for 1 month (Abs. 440) | 2.34 | 8.11 | 8.67 | 12.7 | 13.01 | 15< | 15< | 12.19 | 12.19 | 13.41 |
| Evaluation | ++ | + | + | – | – | – | – | – | – | – |

TABLE 3

| | Comparative Example | | | |
|---|---|---|---|---|
| | 8 | 9 | 10 | 11 |
| Alkali equivalent (g eq.) | 2.0 | | 3.0 | 4.0 |
| Temperature (° C.) | 70 | 80 | 50 | 50 |
| pH (25° C.)* | 13< | 13< | 13< | 13< |
| (1) Hue value (Abs. 440) | 15< | 15< | 1.74 | Solidified |
| Ethanol-insoluble content (mass %) | 9.2 | 9.6 | 16.3 | — |
| Saponification value (mgKOH/g) | 1.92 | 1.75 | 1.99 | — |
| Ignition residue (mass %) | 20.1 | 19.8 | 28.7 | — |
| (2) Hue value after being allowed to stand at 50° C. for 1 month Abs. 440) | 15< | 15< | 15< | Solidified |
| Evaluation | — | — | — | — |

As shown in Tables 1 to 3, the results confirmed that when the composition containing lactonic SL and acidic SL is hydrolyzed under specific temperature conditions by using an alkaline agent in an amount of 0.8 to 1.5 g eq. relative to the saponification value of the composition containing lactonic SL and acidic SL, an acidic SL-containing composition (hydrolysate) with suppressed browning can be obtained wherein a filtrate after hydrolysis of the composition containing lactonic SL and acidic SL has a hue value of 5 or less, and the hue value of the filtrate after storage at 50° C. for 1 month is 10 or less.

The temperature conditions used for hydrolysis can be set according to the gram equivalent of the alkaline agent to be used. Specifically, as shown in Tables 1 to 3, when an alkaline agent is used in an amount of 0.8 g eq. or more but less than 1.0 g eq., preferably 0.8 to 0.9 g eq., the temperature condition is preferably 20 to 80° C. When an alkaline agent is used in an amount of 0.9 to 1.0 g eq., the temperature condition is preferably 20 to 60° C. When an alkaline agent is used in an amount of 1.0 to 1.5 g eq., the temperature condition is preferably 20 to 50° C. When the composition containing lactonic SL and acidic SL is hydrolyzed using an alkaline agent in an amount of 1 g eq. or more relative to the saponification value of the composition, the temperature is preferably 60° C. or less, and more preferably below 50° C.

Additionally, the crudely purified acidic SL-containing product prepared by the method described in Reference Production Example 2 of PTL 2 corresponds to the above composition of Comparative Example 2. To adjust the composition containing lactonic SL and acidic SL prepared in Reference Production Example 1 to a pH of 12, an alkaline agent is necessary in an amount corresponding to 1.0 g eq. The hue value (Abs. 440) of a filtrate of the hydrolysate obtained after treatment at 80° C. for 2 hours in the presence of the alkaline agent was 8.20, which was more than 5. The hue value of the filtrate obtained after 1 month at 50° C. (Abs. 440) was 13.01, which was more than 10. From this, it was confirmed that the obtained product does not correspond to the acidic SL-containing composition of the present invention (hydrolysate of the present invention), which has the feature of browning resistance.

Production Example 2: Preparation of Crudely Purified Acidic SL-Containing Composition (No. 2)

An aqueous solution of sodium hydroxide was added to the composition containing lactonic SL and acidic SL obtained above in Reference Production Example 1 to achieve the gram equivalents shown in Table 4. The composition was treated at the temperature shown in Table 4 for 2 hours to perform alkaline hydrolysis (saponification treatment). After the reaction, the hydrolysate was returned to room temperature (25° C.) and adjusted to a pH of 8 by using a 9.8 M sulfuric acid solution. Subsequently the obtained hydrolysate was filtered through a filter with a pore diameter of 0.45 μm to remove the insoluble matter produced. The resulting filtrate (filtrate of the hydrolysate) was obtained as crudely purified acidic SL-containing compositions (Examples 14 to 17). The crudely purified acidic SL-containing composition contains 78 mass % or more of acidic SL and less than 22 mass % of lactonic SL, when the total of the acidic SL and lactonic SL is defined as 100 mass %.

Using the obtained filtrate of the hydrolysate (crudely purified acidic SL-containing composition) as a test sample, various physical properties (pH, hue value (Abs. 440), ethanol-insoluble content (mass %), saponification value (mgKOH/g), and ignition residue (mass %)) were measured by the methods described above. The filtrate after hydrolysis was further allowed to stand in the dark at 50° C. for one month (30 days). The hue value (Abs. 440) was then measured by the method described above. Table 4 shows the results.

TABLE 4

| | Example | | | |
|---|---|---|---|---|
| | 14 | 15 | 16 | 17 |
| Alkali equivalent (mol) | 0.8 | 1.0 | 1.2 | 1.5 |
| Temperature (° C.) | 40 | 40 | 40 | 40 |
| pH (25° C.) * | 8.0 | 8.0 | 8.0 | 8.0 |
| (1) Hue value (Abs. 440) | 0.90 | 1.30 | 1.34 | 1.00 |
| Ethanol-insoluble content (mass %) | 0.8 | 1.0 | 1.8 | 2.7 |
| Saponification value (mgKOH/g) | 15.21 | 4.22 | 3.71 | 3.62 |
| Ignition residue (mass %) | 9.0 | 10.3 | 12.7 | 15.4 |

TABLE 4-continued

| | Example | | | |
|---|---|---|---|---|
| | 14 | 15 | 16 | 17 |
| (2) Hue value after being allowed to stand at 50° C. for 1 month (Abs. 440) | 1.31 | 1.22 | 1.25 | 1.63 |
| Evaluation | +++ | +++ | +++ | +++ |

As shown in Table 4, the results confirmed that when the composition containing lactonic SL and acidic SL is subjected to alkaline hydrolysis and then adjusted to a pH of 6 to 9, preferably to neutral pH, the hue value can be suppressed to 1.7 or less even after being allowed to stand at 50° C. for 1 month, and the browning phenomenon that progresses over time can be significantly suppressed.

The invention claimed is:

1. A hydrolysate of a composition containing lactonic sophorolipid and acidic sophorolipid, the acidic sophorolipid being present in a proportion of 78 mass % or more, based on the total amount of the lactonic sophorolipid and the acidic sophorolipid taken as 100 mass %, wherein a filtrate of the hydrolysate has the following features (1), (2), (4), (5), and (6):

(1) a hue value of 5 or less, (2) an ethanol-insoluble content of less than 3 mass %, (4) a pH of 6 to 9, (5) a saponification value of 1 to 25 mgKOH/g, and (6) an ignition residue content of 1.3 to 16 mass %, wherein the filtrate of the hydrolysate is a filtrate obtained by adjusting the hydrolysate of the composition containing lactonic sophorolipid and acidic sophorolipid to room temperature 25±5° C. and then filtering the adjusted hydrolysate through a filter with a pore size of 0.45 μm, and wherein the hue value is a value obtained by dissolving the filtrate in distilled water to achieve an ethanol-soluble content of 3 mass %, filtering the diluted aqueous solution through a filter with a pore size of 0.45 μm, measuring the absorbance of the obtained filtrate at a wavelength of 440 nm using an infrared/UV-visible spectrophotometer, and multiplying the absorbance by 10;

with the proviso that the hydrolysate excludes an acidic sophorolipid-composition obtained by hydrolyzing the composition containing lactonic sophorolipid and acidic sophorolipid and then purifying the resulting hydrolysate by column chromatography.

2. The hydrolysate according to claim 1, wherein the filtrate of the hydrolysate further has the following feature (3):

(3) a hue value after being allowed to stand at 50° C. in the dark for 1 month of 10 or less.

3. A method for producing the hydrolysate of claim 1, the method comprising the following steps (a) and (b):

(a) hydrolyzing a composition containing lactonic sophorolipid and acidic sophorolipid under conditions of 80° C. or less using an alkaline agent in an amount of 0.8 to 1.5 g eq. relative to the saponification value of the composition and (b) adjusting the pH of the hydrolyzed composition of step (a) to a pH of 6 to 9 to obtain the hydrolysate.

4. An anionic surfactant comprising the hydrolysate of claim 1 or a processed product thereof as an active ingredient.

5. A perfumery or cosmetic, a food or drink, a detergent, a quasi-drug, a pharmaceutical, or an additive therefor, comprising the hydrolysate of claim 1, or a processed product thereof.

6. A method for producing the perfumery or cosmetic, the food or drink, the detergent, the quasi-drug, or the pharmaceutical of claim 5, the method comprising the steps of mixing a third component for use in the manufacture of perfumery and cosmetics, foods and drinks, detergents, quasi-drugs, or pharmaceuticals into the hydrolysate or a processed product thereof; and forming the resulting mixture into a product.

7. The production method according to claim 3, wherein the filtrate of the hydrolysate further has the following feature (3):

(3) a hue value after being allowed to stand at 50° C. in the dark for 1 month of 10 or less.

* * * * *